(12) United States Patent
Hattori et al.

(10) Patent No.: US 6,303,649 B1
(45) Date of Patent: Oct. 16, 2001

(54) NAPHTHALENE DERIVATIVES

(75) Inventors: Kouji Hattori, Takarazuka; Hiromichi Itani, Hyogo; Akira Tanaka, Takarazuka; Toshifumi Shiraga, Toyonaka, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/582,173

(22) PCT Filed: Dec. 11, 1998

(86) PCT No.: PCT/JP98/05603

§ 371 Date: Aug. 4, 2000

§ 102(e) Date: Aug. 4, 2000

(87) PCT Pub. No.: WO99/32435

PCT Pub. Date: Jul. 1, 1999

(30) Foreign Application Priority Data

Dec. 22, 1997 (AU) ...................................... PP1090

(51) Int. Cl.$^7$ ........................... A61K 31/27; C07C 271/28
(52) U.S. Cl. .............................. 514/476; 560/19; 560/43; 514/510; 514/533; 514/539
(58) Field of Search ................................. 514/476, 510, 514/533, 539, 547; 560/19, 43

(56) References Cited

U.S. PATENT DOCUMENTS

| | | |
|---|---|---|
| 5,763,489 | 6/1998 | Taniguchi et al. . |
| 5,863,918 | 1/1999 | Taniguchi et al. . |
| 5,972,965 | 10/1999 | Taniguchi et al. . |
| 6,025,375 | 2/2000 | Taniguchi et al. . |

FOREIGN PATENT DOCUMENTS

WO95/24393  9/1995  (WO) .

*Primary Examiner*—C S. Aulakh
(74) *Attorney, Agent, or Firm*—Oblon, Spivak, McClelland, Maier & Neustadt, P.C.

(57) ABSTRACT

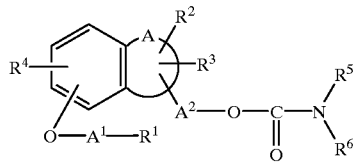

(I)

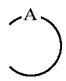

(II)

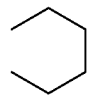

(III)

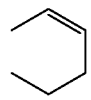

(IV)

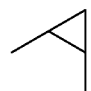

(V)

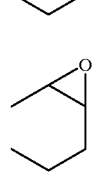

(VI)

A compound of formula (I), wherein $R^1$ is carboxy or protected carboxy, $R^2$ and $R^3$ are each independently hydrogen, hydroxy, or protected hydroxy, $R^4$ is hydrogen or halogen, $R^5$ is aryl substituted with halogen, amino, hydroxy or protected hydroxy, $R^6$ is aryl optionally substituted with halogen, amino, hydroxy or protected hydroxy, $A^1$ and $A^2$ are each independently lower alkylene, and (II) is (III), (IV), (V) or (VI) or its salt, process for preparing it, a pharmaceutical composition including it, and a use thereof.

12 Claims, No Drawings

NAPHTHALENE DERIVATIVES

TECHNICAL FIELD

This invention relates to new naphthalene derivatives and pharmaceutically acceptable salts thereof which are useful as a medicament.

BACKGROUND ART

Some compounds having pharmacological activities such as an inhibitory activity on platelet aggregation have been known, for example, in WO 95/17393, WO 95/24393, WO 97/03973, EP 0 542 203, U.S. Pat. No. 5,362,879.

DISCLOSURE OF INVENTION

This invention relates to new naphthalene derivatives. More particularly, this invention relates to new naphthalene derivatives and pharmaceutically acceptable salts thereof which have pharmacological activities such as an inhibitory activity on platelet aggregation, vasodilating activity, antihypertensive activity or the like and are prostaglandin $I_2$ (hereinafter referred as $PGI_2$) agonists, to processes for their production, to a pharmaceutical composition containing the same and to a use thereof for manufacture of medicaments.

Accordingly, one object of this invention is to provide new and useful naphthalene derivatives and pharmaceutically acceptable salts thereof.

Another object of this invention is to provide processes for production of the naphthalene derivatives and salts thereof.

A further object of this invention is to provide a pharmaceutical composition containing, as an active ingredient, said naphthalene derivatives or pharmaceutically acceptable salts thereof.

Still further object of this invention is to provide a use of the naphthalene derivatives and pharmaceutically acceptable salts thereof for manufacture of medicaments for the therapeutic and/or prophylactic treatment of arterial obstruction, cerebrovascular disease, hepatic cirrhosis, arteriosclerosis, ischemic heart disease, restenosis or ischemic complications after coronary angioplasty, hypertension, inflammatory bowel disease, dermatosis or the like.

The naphthalene derivatives of this invention can be represented by the following formula (I).

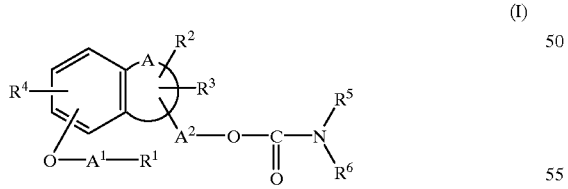

(I)

wherein
   $R^1$ is carboxy or protected carboxy,
   $R^2$ and $R^3$ are each independently hydrogen, hydroxy or protected hydroxy,
   $R^4$ is hydrogen or halogen,
   $R^5$ is aryl substituted with halogen, hydroxy or protected hydroxy,
   $R^6$ is aryl optionally substituted with halogen, hydroxy or protected hydroxy, $A^1$ and $A^2$ are each independently lower alkylene, and

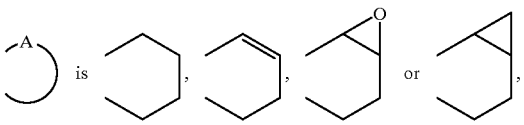

and its salt.

According to the present invention, the new naphthalene derivatives (I) can be prepared by the processes which are illustrated in the following scheme.

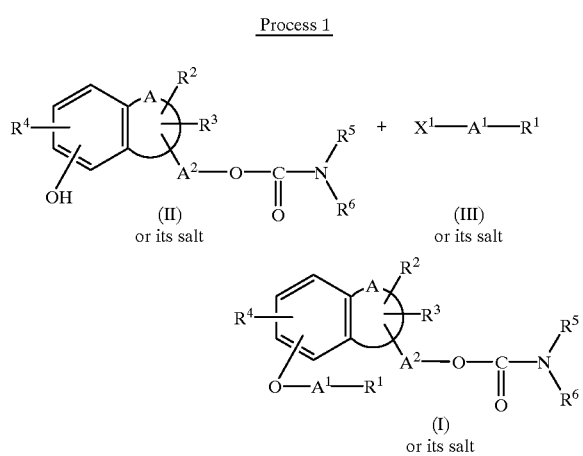

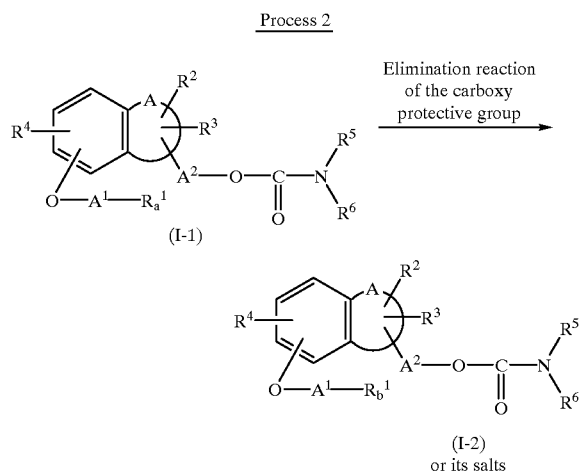

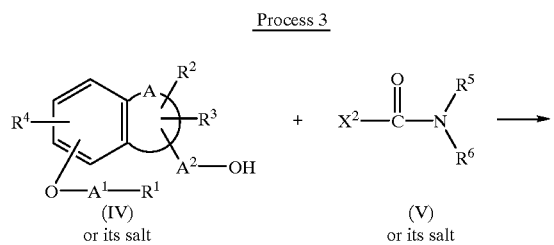

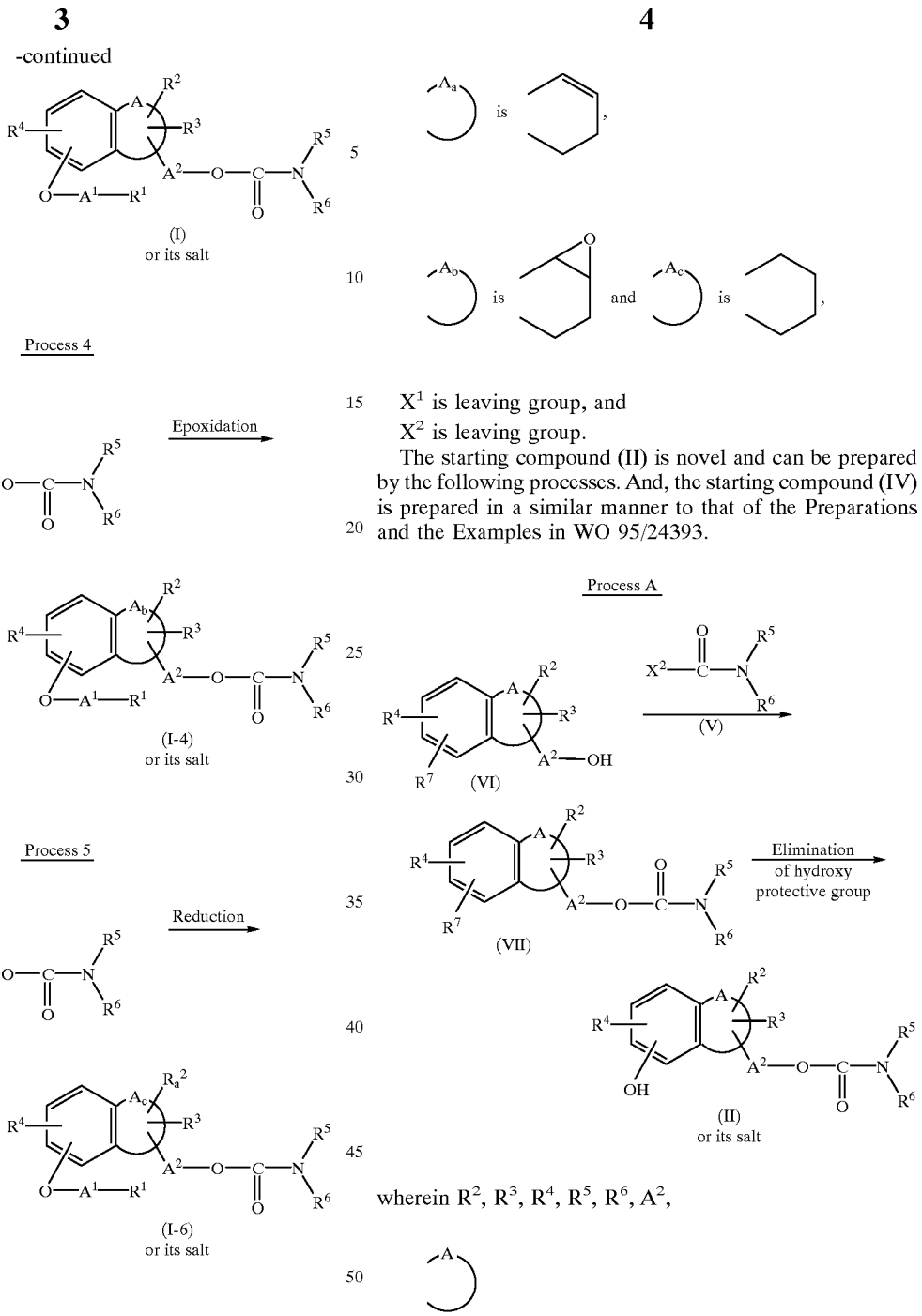

Process 4

(I-3) or its salt → Epoxidation → (I-4) or its salt

Process 5

(I-5) or its salt → Reduction → (I-6) or its salt wherein $R^1$, $R^2$, $R^3$, $R^4$, $R^5$, $R^6$, $A^1$, $A^2$ and

are each as defined above, $R_a^1$ is protected carboxy,
$R_b^1$ is carboxy,
$R_a^2$ is hydroxy, $A_a$ is cyclohexenyl, $A_b$ is epoxycyclohexyl and $A_c$ is cyclohexyl, $X^1$ is leaving group, and
$X^2$ is leaving group.

The starting compound (II) is novel and can be prepared by the following processes. And, the starting compound (IV) is prepared in a similar manner to that of the Preparations and the Examples in WO 95/24393.

Process A (VI) + (V) → (VII) → Elimination of hydroxy protective group → (II) or its salt wherein $R^2$, $R^3$, $R^4$, $R^5$, $R^6$, $A^2$, $A$ and $X^2$ are each as defined above, $R^7$ is protected hydroxy.

Suitable pharmaceutically acceptable salts of the object compounds (I) and (I-1) to (I-6), and the compounds (II) to (V) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, trifluoroacetate, etc.), an inorganic acid salt (e.g.

hydrochloride, hydrobromide, sulfate, phosphate, etc.), a salt with an amino acid (e.g. arginine, aspartic acid, glutamic acid, etc.), and the like.

It is to be noted the object compound (I) may include one or more stereoisomers due to asymmetric carbon atom(s) and double bond, and all of such isomers and a mixture thereof are included within the scope of the present invention.

It is further to be noted isomerization or rearrangement of the object compound (I) may occur due to the effect of the light, acid, base or the like, and the compound obtained as the result of said isomerization or rearrangement is also included within the scope of the present invention.

It is also to be noted that the solvating form of the compound (I) (e.g. hydrate, etc.) and any form of the crystal of the compound (I) are included within the scope of the present invention.

Also included in the scope of the invention are radiolabeled derivatives of the compound of the formula (I) which are suitable for biological studies.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "aryl" may include phenyl, tolyl, xylyl, mesityl, naphthyl and the like.

Suitable "lower alkylene" may include straight or branched one having 1 to 6 carbon atom(s), such as methylene, ethylene, trimethylene, tetramethylene, pentamethylene, hexamethylene or the like, preferably one having 1 to 3 carbon atom(s).

Suitable "lower alkyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atom(s).

Suitable "protected carboxy" may include esterified carboxy and the like.

Suitable example of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, etc.], halo(lower)alkyl ester (e.g. 2-iodoethyl ester, 2,2,2-trichloroethyl ester, etc.), or lower alkoxycarbonyloxy(lower)alkyl ester (e.g. methoxycarbonyloxymethyl ester, 2-methoxycarbonyloxyethyl ester, etc.); lower alkenyl ester (e.g. vinyl ester, allyl ester, etc.); lower alkynyl ester (e.g. ethynyl ester, propynyl ester, etc.); ar (lower)alkyl ester which may have at least one suitable substituent(s) such as phenyl(lower)alkyl ester which may have at least one suitable substituent(s) (e.g. benzyl ester, 4-methoxybenzyl ester, 4-nitrobenzyl ester, phenethyl ester, trityl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, ethylphenyl ester, propylphenyl ester, tert-butylphenyl ester, xylyl ester, mesityl ester, cumenyl ester, etc.); and the like.

Suitable "protected hydroxy" may include lower alkoxy, acyloxy, tri(lower) alkylsilyloxy, diaryl(lower)alkylsilyloxy, and the like. Suitable examples of said "lower alkoxy" may include methoxy, ethoxy, tert-butoxy, and the like. Suitable "acyl moiety" in said "acyloxy" may include aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, etc.); lower alkylsulfonyl (e.g. mesyl, ethanesulfonyl, etc.); arylsulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.); and the like. Suitable example of tri(lower)alkylsilyl moiety in said "tri(lower)alkylsilyloxy" may include trimethylsilyl, triethylsilyl, triisopropylsilyl, dimethylisopropylsilyl, tert-butyldimethylsilyl, and the like. Suitable example of diaryl (lower)alkylsilyl moiety in said "diaryl(lower) alkylsilyloxy" may include tert-butyldiphenylsilyl, and the like.

Suitable "leaving group" may include halogen, lower alkoxy (e.g., methoxy, ethoxy, propoxy, isopropoxy, butoxy, etc.), acyloxy as exemplified above, and the like.

Suitable "halogen" may include chlorine, bromine, iodine and fluorine.

Preferred embodiments of the object compound (I) are as follows:

$R^1$ is carboxy, or protected carboxy (more preferably esterified carboxy, most preferably lower alkoxycarbonyl), $R^2$ is hydrogen or hydroxy, $R^3$ is hydrogen or hydroxy, $R^4$ is hydrogen or halogen (more preferably hydrogen), $R^5$ is aryl (more preferably phenyl) substituted with halogen or hydroxy (more preferably, halogen, most preferably fluoro), $R^6$ is aryl (more preferably phenyl) optionally substituted with halogen (more preferably fluoro), $A^1$ is lower alkylene (more preferably $C_1$–$C_3$ alkylene, most preferably methylene), $A^2$ is lower alkylene (more preferably $C_1$–$C_3$ alkylene, most preferably methylene), and

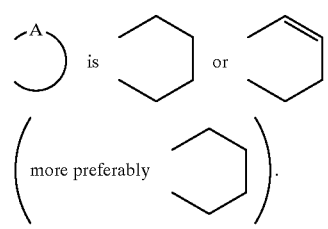

The processes for preparing the object and starting compounds of the present invention are explained in detail in the following.

Process 1

The compound (I) or its salt can be prepared by reacting the compound (II) or its salt with the compound (III) or its salt.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to heating.

The reaction is usually carried out in the presence of a base.

Suitable base may include the inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkali metal bicarbonate (e.g. sodium bicarbonate, potassium bicarbonate, etc.), alkaline earth metal carbonate (e.g. magnesium carbonate, calcium carbonate, etc.) or the like, and the organic base such as tri(lower)alkylamine (e.g., trimethylamine, triethylamine, diisopropylethylamine, etc.), di(lower)alkylaniline (e.g. dimethylaniline, etc.), pyridine or the like.

Process 2

The compound (I-2) or its salt can be prepared by subjecting the compound (I-1) or its salt to elimination reaction of the carboxy protective group.

Suitable method of this reaction may include conventional one such as hydrolysis, reduction and the like.

(i) For Hydrolysis

The hydrolysis is preferably carried out in the presence of a base or an acid including Lewis acid.

Suitable base may include an inorganic base and an organic base such as an alkali metal [e.g. sodium, potassium, etc.], the hydroxide or carbonate or bicarbonate thereof, trialkylamine [e.g. trimethylamine, triethylamine, etc.], picoline, 1,5-diazabicyclo[4.3.0]-non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, 1,2-dimethoxyethane, dioxane, a mixture thereof or any other solvent which does not adversely influence the reaction. A liquid base or acid can be also used as the solvent. The reaction temperature is not critical and the reaction is usually carried out under cooling to warming.

(ii) For Reduction

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (eg. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, N,N-dimethylformamide, tetrahydrofuran, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

Process 3

The compound (I) or its salt can be prepared by reacting the compound (IV) or its salt with the compound (V) or its salt.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to heating.

The reaction is usually carried out in the presence of a base.

Suitable base can be referred to that of Process 1. A liquid base can be also used as the solvent.

Process 4

The compound (I-4) or its salt can be prepared by subjecting a compound (I-3) or its salt to an epoxidation.

Epoxidation of alkene is accomplished by oxidants, for example, hydrogen peroxide or its derivatives. Suitable derivatives of the hydrogen peroxide are lower alkyl hydroperoxide (e.g., tert-butyl hydroperoxide, etc.), peroxy acid (e.g., peroxyacetic acid, peroxytrifluoroacetic acid, m-chloroperoxybenzoic acid, etc.), or the like. Other oxidants used for epoxidation are dimethyldioxirane, ozone, sodium hypochlorite, or the like.

This reaction preferably carried out in the presence of base such as an inorganic base and an organic base such as an alkali metal [e.g. sodium, potassium, etc.], the hydroxide or carbonate or bicarbonate thereof, trialkylamine [e.g. trimethylamine, triethylamine, etc.], or the like.

The reaction is usually carried out in a conventional solvent such as water, alcohol (e.g., methanol, ethanol, isopropyl alcohol, etc.), tetrahydrofuran, dioxane, dichloromethane, ethylene dichloride, chloroform, N,N-dimethylformamide, N,N-dimethylacetamide, or any other organic solvent which does not adversely affect the reaction.

The reaction temperature is not critical and the reaction is usually carried out under cooling to heating.

Process 5

A compound (I-6) or its salt can be prepared by reducing a compound (I-5) or its salt.

Reduction of epoxide is accomplished by (1) catalytic hydrogenation over platinum catalyst, preferably in the presence of acid, or (2) chemical reduction using complex hydride, such as lithium alminin hydride, alanes or borans.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to heating.

Process A

The compound (II) or its salt can be prepared by subjecting the compound (XII) to carbamoylation, followed by elimination of hydroxy protective group.

These reactions can be carried out in accordance with the methods disclosed in the Preparations 1 and 2 or similar manners thereto.

The object compound (I) of this invention and pharmaceutically acceptable salt thereof have pharmacological activities such as an inhibitory activity on platelet aggregation, vasodilating activity, antihypertensive activity or the like and are prostaglandin $I_2$ agonist, and therefore can be used for treating and/or preventing thrombosis, arterial obstruction (e.g., chronic arterial obstruction, etc.), cerebrovascular disease, gastric ulcer, hepatitis, hepatic insufficiency, hepatic cirrhosis, arteriosclerosis, ischemic heart disease, restenosis or ischemic complications after coronary angioplasty (e.g., PTCA, coronary stenting, etc.) hypertension, inflammation, heart failure, renal disease (e.g., renal failure, nephritis, etc.), diabetic complication (e.g., diabetic neuropathy, diabetic nephropathy, diabetic retinopathy, etc.), peripheral circulatory disturbance, inflammatory bowel disease {such as specific inflammatory bowel disease [e.g., infectious enteritis, drug induced colitis (e.g., antibiotics associated colitis, etc.), ischemic colitis, etc.], idiopathic inflammatory bowel disease (e.g., ulcerative colitis, Crohn's disease, etc.) and the like}, and the like, and can be also used for protecting organs after transplantation or surgery.

Further, the object compound (I) and pharmaceutically acceptable salt thereof can be also used as a component for organ preserving fluids and as an agent for inhibiting metastasis of cancer.

Still further, the compounds having $PGI_2$ agonizing activity, which are described in this application and WO 95/17393, WO 95/24393, WO 97/03973 etc., are also useful for treating and/or preventing of dermatosis (e.g., chilblain, bedsore, baldness, etc.).

The compound (I) of the present invention has much advantage, such as stronger activity, more suitable half-life, decreased adverse effect, or the like, compared to the known compounds shown in the prior arts.

The patents, patent applications and publications cited herein are incorporated by reference.

In order to show the utility of the object compound (I), pharmacological data of the representative compounds thereof are shown in the following.

i) Inhibition of Human Platelet Aggregation Induced by ADP

[I] Test Compound (1) Sodium {{(2R)-2-{[N,N-di(4-fluorophenyl) carbamoyloxy]-methyl}-2-hydroxy-1,2,3,4tetrahydro-5-naphthyl}oxy}-acetate

[II] Test Method

Human blood was obtained from healthy volunteers and mixed with 1/10 volume of 3.8% sodium citrate, pH 7.4. The citrate blood was centrifuged at 150×g for 10 minutes and the platelet rich plasma (PRP) was removed. The remaining blood was centrifuged for a further 10 minutes at 1500×g to prepare the platelet poor plasma (PPP), which was used as a reference for platelet aggregation. Aggregation studies were carried out using HEMATBACER 801 (NBS, Japan), a 8 channel aggregometer. 25 μl of sample solution and 225 μl of PRP were mixed and stirred at 1000 rpm for 2 minutes at 37° C. Aggregation was induced by ADP (adenosin 5'-diphosphate) solution at the final concentration of 2.5 μM.

[III] Test result

| Test compound $(1.0 \times 10^7 M)$ | Inhibition (%) |
|---|---|
| (1) | >85% |

The pharmaceutical composition of the present invention can be used in the form of a pharmaceutical preparation, for example, in solid, semisolid or liquid form (e.g. tablet, pellet, troche, capsule, suppository, cream, ointment, aerosol, powder, solution, emulsion, suspension etc.), which contains the object compound (I) or a pharmaceutically acceptable salt thereof as an active ingredient, suitable for rectal, pulmonary (nasal or buccal inhalation), nasal, ocular, external (topical), oral or parenteral (including subcutaneous, intravenous and intramuscular) administrations or insufflation.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (e.g. cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycol-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

Abbreviations used in this application are as follows:

| | |
|---|---|
| THF | Tetrahydrofuran |
| AcOEt | Ethyl acetate |
| $Et_2O$ | Diethyl ether |
| DMF | N,N-Dimethylformamide |
| EtOH | Ethyl alcohol |
| MeOH | Methyl alcohol |
| TMS | Trimethylsilyl |
| AcOH | Acetic acid |

The following preparations and examples are given only for the purpose of illustrating the present invention in more detail.

Preparation 1

A mixture of (2R)-5-t-butyldiphenylsiloxy-2-hydroxy-2-(hydroxymethyl)-1,2,3,4-tetrahydronaphthalene (0.49 g) and N,N-di(4-fluorophenyl)carbamoyl chloride (1.08 g) in pyridine (2.3 ml) was stirred at 100° C. for 1.5 hours. The reaction mixture was partitioned between ethyl acetate and water. The organic layer was washed with water, 1N-HCl, and evaporated in vacuo. The residue was purified by chromatography on silica gel (50 ml) using a mixture of AcOEt and n-hexane to give (2R)-5-t-butyldiphenylsiloxy-2-{[N,N-di(4-fluorophenyl)-carbamoyloxy]methyl}-2-hydroxy-1,2,3,4-tetrahydronaphthalene (0.356 g) as an oil.

IR (Neat): 3430, 1700, 1580 cm$^{-1}$

NMR (CDCl$_3$, δ): 1.10 (9H, s), 1.73–1.88 (2H, m), 2.0–2.15 (1H, m), 2.73 (2H, d, J=3.4 Hz), 2.88–2.96 (2H, m), 4.17 (1H, s), 6.26 (1H, d, J=7.0 Hz), 6.54 (1H, d, J=7.0 Hz), 6.70 (1H, t, J=7.8 Hz), 7.01–7.10 (4H, m), 7.21–7.42 (10H, m), 7.66–7.72 (4H, m)

Mass: 664 (M+H)$^+$

Preparation 2

To a mixture of (2R)-5-t-butyldiphenylsiloxy-2-{[N,N-di(4-fluorophenyl)carbamoyloxy]methyl}-2-hydroxy-1,2,3,4-tetrahydronaphthalene in THF (1 ml) was added 1M-tetra-n-butylammonium fluoride solution in THF (0.77 ml) at room temperature. After stirring for 4 hours, the reaction mixture was partitioned between AcOEt and water. The organic layer was washed with 1N-HCl, water, and evaporated in vacuo. The residue was purified by chromatography on silica gel (25 ml) using a mixture of AcOEt and n-hexane (1:4) to give (2R)-2-{[N,N-di(4-fluorophenyl) carbamoyloxy]methyl}-2,5-dihydroxy-1,2,3,4-tetrahydronaphthalene (0.19 g) as an oil.

IR (Neat): 3350, 1700, 1580 cm$^{-1}$

NMR (CDCl$_3$, δ): 1.63–1.87 (2H, m), 2.60–2.84 (4H, m), 4.17 (2H, s), 4.92 (1H, s), 6.57–6.62 (2H, m), 6.96–7.10 (4H, m), 7.19–7.28 (5H, m)

Mass: 426 (M+H)$^+$

Preparation 3

To a solution of 3-chlorodiphenylamine (3.0 g) and pyridine (1.43 mL) in CH2Cl2 (30 mL) was added triphosgene (1.75 g) at 5° C. After stirring at room temperature for 6 hours, the mixture was evaporated, diluted with EtOAc, washed with water and brine, dried over magnesium sulfate, and evaporated in vacuo. The residue was purified by silica gel column chromatography (hexane-EtOAc 15:1) to give N-(3-chlorophenyl)-N-phenylcarbamoyl chloride (4.05 g) as an oil.

IR (neat): 3068, 1741, 1589, 1491, 1475, 1273 cm$^{-1}$

NMR (DMSO-d$_6$, δ): 7.20–7.98 (9H, m)

ESI-MS m/z 288, 290, 292 (M+Na)$^+$

EXAMPLE 1

To a mixture of (2R)-2-{[N,N-di(4-fluorophenyl)-carbamoyloxy]methyl}-2,5-dihydroxy-1,2,3,4-tetrahydronaphthalene (0.18 g) and powder K$_2$CO$_3$ in dry DMF (1.8 ml) was added ethyl bromoacetate (0.047 ml) at room temperature. After stirring for 16 hours, the reaction mixture was partitioned between AcOEt and water. The organic layer was washed with water, brine, dried over MgSO$_4$ and evaporated in vacuo. The residue was crystallized from n-hexane to give (2R)-2-{[N,N-di(4-flurophenyl) carbamoyloxy]methyl}-5-[(ethoxycarbonyl)methoxy]-2-hydroxy-1,2,3,4-tetrahydronaphthalene (0.16 g) as white solid.

IR (Neat): 3460, 1750, 1690, 1600, 1580 cm$^{-1}$

NMR (CDCl$_3$, δ): 1.30 (3H, t, J=7.1 Hz), 1.65–1.85 (2H, m), 2.72 (2H, s), 2.78–2.88 (2H, m), 4.15 (2H, s), 4.26 (2H, q, J=7.1 Hz), 4.61 (2H, s), 6.54 (1H, d, J=8.4 Hz), 6.67 (1H, d, J=7.6 Hz), 7.00–7.10 (4H, m), 7.19–7.28 (5H, m)

Mass: 512 (M+H)$^+$

EXAMPLE 2

To a solution of N-(4-fluorophenyl)aniline (1.1 g) and pyridine (0.6 ml) in dichloromethane (20 ml) was added triphosgen (0.61 g) at 0° C. After being stirred for 4 hours at the room temperature, the solution was evaporated in vacuo. The obtained oil was dissolved into pyridine (5 ml) and (2R)-2-hydroxy-2-(hydroxymethyl)-5-[(ethoxycarbonyl)-methoxy]-1,2,3,4-tetrahydronaphthalene (1.1 g) was added to the solution. The mixture was stirred for 8 hours at 100° C. and partitioned between ethyl acetate and water. The organic layer was washed with 1N-HCl, sat. NaHCO$_3$, and brine. The dried solvent was evaporated in vacuo and the residue was purified by chromatography on silica gel to give (2R)-2-[(N-4-fluorophenyl-N-phenylcarbamoyloxy)methyl]-5-[(ethoxycarbonyl)methoxy]-2-hydroxy-1,2,3,4-tetrahydro-naphthalene (90 mg).

IR (Neat): 3400, 1756, 1712 cm$^{-1}$

NMR (CDCl$_3$, δ): 1.29 (3H, t, J=7 Hz), 1.6–2.0 (2H, m), 2.6–3.0 (4H, m), 4.14 (2H, s), 4.24 (2H, q, J=7 Hz), 4.60 (2H, s), 6.53 (1H, d, J=8 Hz), 6.66 (1H, d, J=8 Hz), 7.0–7.5 (10H, m)

Mass: 476 (M−H$_2$O)$^+$

EXAMPLE 3

The following compounds (1) to (5) were obtained according to a similar manner to that of Example 2.

(1) (2R)-2-[(N-4-Bromophenyl-N-phenylcarbamoyloxy) methyl]-5-[(ethoxycarbonyl)methoxy]-2-hydroxy-1,2,3,4-tetrahydronaphthalene IR (Neat): 3400, 1756, 1716 cm$^{-1}$ NMR (CDCl$_3$, δ): 1.29 (3H, t, J=7 Hz), 1.6–2.0 (2H, m), 2.6–3.0 (4H, m), 4.06 (2H, s), 4.24 (2H, q, J=7 Hz), 4.60 (2H, s), 6.53 (1H, d, J=8 Hz), 6.66 (1H, d, J=8 Hz), 7.0–7.5 (10H, m)

Mass: 554 (M$^+$)

(2) (2R)-2-[(N-3-Fluorophenyl-N-4-fluorophenylcarbamoyloxy)methyl]-5-[(ethoxycarbonyl) methoxy]-2-hydroxy-1,2,3, 4-tetrahydronaphthalene IR (Neat): 3400. 1756, 1716 cm$^{-1}$ NMR (CDCl$_3$, δ): 1.29 (3H, t, J=7 Hz), 1.6–2.0 (2H, m), 2.6–3.0 (4H, m), 4.06 (2H, s), 4.24 (2H, q, J=7 Hz), 4.60 (2H, s), 6.53 (1H, d, J=8 Hz), 6.66 (1H, d, J8 Hz), 6.95 (1H, t, J=8 Hz), 7.0–7.4 (8H, m)

Mass: 512 (M$^+$)

(3) (2R)-2-[(N-2-Fluorophenyl-N-4-fluorophenylcarbamoyloxy)-methyl]-5-[(ethoxycarbonyl) methoxy]-2-hydroxy-1,2,3,4-tetrahydronaphthalene IR (Neat): 3400, 1752, 1718 cm$^{-1}$ NMR (CDCl$_3$, δ): 1.29 (3H, t, J=7 Hz), 1.6–2.0 (2H, m), 2.6–3.0 (4H, m), 4.06 (2H, s), 4.24 (2H, q, J=7 Hz), 4.60 (2H, s), 6.53 (1H, d, J=8 Hz), 6.66 (1H, d, J=8 Hz), 7.0–7.4 (9H, m)

Mass: 512 (M$^+$)

(4) (2R)-2-{[N,N-di(3-Fluorophenyl)carbamoyloxy] methyl}-5-[(ethoxycarbonyl)methoxyl-2-hydroxy-1,2,3,4-tetrahydronaphthalene IR (Neat): 3480, 1756, 1722 cm$^{-1}$ NMR (CDCl$_3$, δ): 1.29 (3H, t, J=7 Hz), 1.6–2.0 (2H, m), 2.6–3.0 (4H, m), 4.10 (2H, s), 4.24 (2H, q, J=7 Hz), 4.61 (2H, s), 6.53 (1H, d, J=8 Hz), 6.66 (1H, d, J=8 Hz), 7.0–7.4 (9H, m)

Mass: 494 (M−H$_2$O+H)$^+$ (5) (2R)-2-{[(N,N-di(2-Fluorophenyl)carbamoyloxy) methyl]-5-[(ethoxycarbonyl)methoxy]-2-hydroxy-1,2,3,4-tetrahydronaphthalene IR (Neat): 3498, 1754, 1727cm$^{-1}$ NMR (CDCl$_3$, δ): 1.29 (3H, t, J=7 Hz), 1.6–2.0 (2H, m), 2.6–3.0 (4H, m), 4.10 (2H, s), 4.24 (2H, q, J=7 Hz), 4.63 (2H, s), 6.53 (1H, d, J=8 Hz), 6.66 (1H, d, J=8 Hz), 7.0–7.4 (9H, m)

Mass: 494 (M−H$_2$O+H)$^+$

EXAMPLE 4

A solution of (2R)-2-{[N,N-di(4-fluorophenyl)-carbamoyloxy]methyl}-5-[(ethoxycarbonyl)methoxy]-2-hydroxy-1,2,3,4-tetrahydronaphthalene (0.155 g) and 1N-NaOH (0.286 ml) in MeOH (1.5 ml) was stirred for 16 hours at room temperature. After evaporating in vacuo, the residue was crystallized from ether to give sodium {{(2R)-2-{[N,N-di(4-fluorophenyl)carbamoyloxy]methyl}-2-hydroxy-1,2,3,4-tetrahydro-5-naphthyl}oxy}acetate (sodium salt of (2R)-5-(carboxymethoxy)-2-{[N,N-di(4-fluorophenyl)carbamoyloxy]methyl}-2-hydroxy-1,2,3,4-tetrahydronaphthalene) (111 mg) as white solid.

IR (Nujol): 1700, 1590, 1500 cm$^{-1}$

NMR (DMSO-d$_6$, δ): 1.20–1.70 (2H, m), 2.49–2.60 (4H, m), 3.98 (2H, s), 4.08 (2H, s), 4.65 (1H, s), 6.43–6.50 (2H, m), 6.92 (1H, t, J=7.1 Hz), 7.16–7.25 (4H, m), 7.34–7.41 (4H, m)

Mass: 484 (M+H)$^+$

Anal. Calcd. for C$_{26}$H$_{22}$F$_2$NO$_6$Na.2.5H2O: C 56.73, H 4.94, N 2.54

Found C 56.87, H 4.85, N 2.28

EXAMPLE 5

To a solution of (2R)-5-[(ethoxycarbonyl)methoxy]-2-[(N-4-fluorophenyl-N-phenylcarbamoyloxy)methyl]-2-hydroxy-1,2,3,4-tetrahydronaphthalene (80 mg) in ethanol (5 ml) was added 1N-NaOH solution (0.2 ml). After being stirred for 4 hours at the same temperature, the solvent was removed in vacuo. The residue was washed with 1N-HCl solution and brine. The dried solvent was removed in vacuo to give (2R)-5-(carboxymethoxy)-2-[(N-4-fluorophenyl-N-phenyl-carbamoyloxy)methyl]-2-hydroxy-1,2,3,4-tetrahydronaphthalene (32 mg).

IR (CHCl$_3$): 3400, 1710, 1580 cm$^{-1}$

NMR (DMSO-d$_6$, δ): 1.4–1.6 (2H, m), 2.4–2.8 (4H, m), 3.97 (2H, s), 4.07 (2H, s), 6.43 (1H, d, J=8 Hz), 6.52 (1H, d, J=8 Hz), 6.91 (1H, t, J=8 Hz), 7.0–7.4 (9H, m)

Mass: 488 (M+H)$^+$

EXAMPLE 6

The following compounds (1) to (6) were prepared according to a similar manner to that of Example 5.

(1) (2R)-2-[(N-4-Bromophenyl-N-phenylcarbamoyloxy)methyl]-5-(carboxymethoxy)-2-hydroxy-1,2,3,4-tetrahydronaphthalene IR (CHCl$_3$): 3400, 1714, 1587 cm$^{-1}$ NMR (CDCl$_3$, δ): 1.6–2.0 (2H, m), 2.7 (2H, s), 2.6–2.9 (2H, m), 4.15 (2H, s), 4.65 (2H, s), 6.56 (1H, d, J=8 Hz), 6.69 (1H, d, J=8 Hz), 7.08 (1H, t, J=8 Hz), 7.0–7.6 (9H, m)

Mass: 508 (M–H$_2$O)$^+$ (2) (2R)-5-(Carboxymethoxy)-2-[(N-4-fluorophenyl-N-3-fluorophenylcarbamoyloxy)methyl]-2-hydroxy-1,2,3,4-tetrahydronaphthalene IR (CHCl$_3$): 3400, 1714, 1610, 1590 cm$^{-1}$ NMR (CDCl$_3$, δ): 1.6–2.0 (2H, m), 2.7 (2H, s), 2.6–2.9 (2H, m), 4.16 (2H, s), 4.65 (2H, s), 6.57 (1H, d, J=8 Hz), 6.69 (1H, d, J=8 Hz), 6.93 (1H, t, J=8 Hz), 6.9–7.4 (8H, m)

Mass: 466 (M–H$_2$O+H)$^+$ (3) (2R)-5-(Carboxymethoxy)-2-[(N-4-fluorophenyl-N-2-fluorophenylcarbamoyloxy)methyl]-2-hydroxy-1,2,3,4-tetrahydronaphthalene IR (CHCl$_3$): 3400, 1720, 1604, 1587 cm$^{-1}$ NMR (CDCl$_3$, δ): 1.6–2.0 (2H, m), 2.7 (2H, s), 2.6–2.9 (2H, m), 4.17 (2H, s), 4.65 (2H, s), 6.57 (1H, d, J=8 Hz), 6.69 (1H, d, J=8 Hz), 7.0–7.4 (9H, m)

Mass: 466 (M–H$_2$O+H)$^+$ (4) (2R)-5-(Carboxymethoxy)-2-{[N,N-di(3-fluorophenyl)-carbamoyloxy]methyl}-2-hydroxy-1,2,3,4-tetrahydronaphthalene IR (CHCl$_3$): 3400, 1724, 1710 cm$^{-1}$ NMR (DMSO-d$_6$, δ): 1.4–1.9 (2H, m), 2.4–2.9 (4H, m), 4.00 (2H, s), 4.17 (2H, s), 6.46 (1H, d, J=8 Hz), 6.55 (1H, d, J=8 Hz), 6.8–7.4 (9H, m)

Mass: 466 (M–H$_2$O+H)$^+$ (5) (2R)-5-(Carboxymethoxy)-2-{[N,N-di(2-fluorophenyl)-carbamoyloxy]methyl}-2-hydroxy-1,2,3,4-tetrahydronaphthalene IR (CHCl$_3$): 3434, 1724, 1608 cm$^{-1}$ NMR (CDCl$_3$, δ): 1.6–2.0 (2H, m), 2.6–3.0 (4H, m), 4.19 (2H, s), 4.65 (2H, s), 6.57 (1H, d, J=8 Hz), 6.71 (1H, d, J=8 Hz), 7.0–7.4 (9H, m)

Mass: 466 (M–H$_2$O+H)$^+$

EXAMPLE 7

A mixture of (2R)-2-hydroxy-2-(hydroxymethyl)-5-[(ethoxy carbonyl)methoxy]-1,2,3,4-tetrahydronaphthalene (465 mg) and N-(3-chlorophenyl)-N-phenylcarbamoyl chloride (2.21 g) in pyridine (10 mL) was stirred at 100° C. for 24 hours. After cooling, the reaction mixture was poured into 3N hydrochloric acid (50 mL) under ice-cooling and extracted with EtOAc The organic layer was washed with water, saturated sodium hydrogen carbonate, water, and brine, dried over magnesium sulfate, evaporated in vacuo. The residue was purified by silica gel column chromatography (hexane-EtOAc 3:2) to give (2R)-2-{N-(3-chlorophenyl)-N-phenylcarbamoyloxy]methyl}-5-[(ethoxycarbonyl)methoxy]-2-hydroxy-1,2,3,4-tetrahydronaphthalene (800.6 mg) as a solid.

IR (KBr): 3489, 1763, 1693, 1589, 1473 cm$^{-1}$

NMR (CDCl$_3$, δ): 1.30 (3H, t, J=7.2 Hz), 1.60–1.90 (2H, m), 1.99 (1H, s), 2.60–2.95 (4H, m), 4.16 (2H, s), 4.26 (2H, q, J=7.2 Hz), 4.61 (2H, s), 6.54 (1H, d, J=7.8 Hz), 6.68 (1H, d, J=7.8 Hz), 7.06 (1H, dd, J=7.8, 7.8 Hz), 7.12–7.45 (9H, m)

ESI–MS m/z 532, 534 (M+Na)$^+$

EXAMPLE 8

To a solution of (2R)-2-{N-(3-chlorophenyl)-N-phenylcarbamoyloxy]methyl}-5-[(ethoxycarbonyl)methoxy]-2-hydroxy-1, 2,3,4-tetrahydronaphthalene (531 mg) in EtOH-THF (2:1, 9.6 mL) was added 1N sodium hydroxide solution (1.25 mL) at 5° C. and the mixture was stirred at the same temperature for 3 hours. To the reaction mixture was added water (2 mL), and the mixture was evaporated. To the residue was added 1N hydrochloric acid (1.35 mL) under ice-cooling and extracted with EtOAc. The organic layer was washed with water and brine, dried over magnesium sulfate, and evaporated in vacuo. The residue was purified by silica gel column chromatography (CH2Cl2-MeOH 5:1) and recrystallized from EtOH-Et20-hexane to give (2R)-2-{[N-(3-chlorophenyl)-N-phenylcarbamoyloxy]-methyl}-5-(carboxymethoxy)-2-hydroxy-1,2,3,4-tetrahydronaphthalene (331.4 mg).

IR (KBr): 3504, 3483, 3066, 2910, 1751, 1693, 1587, 1471, 1406 cm$^{-1}$

NMR (DMSO-d$_6$, δ): 1.38–1.75 (2H, m), 2.38–2.72 (4H, m), 4.01 (2H, s), 4.64 (2H, s), 4.55–4.73 (1H, br), 6.50–6.65 (2H, m), 7.01 (1H, dd, J=7.8, 7.8 Hz), 7.13–7.53 (9H, m)

ESI–MS (negative mode) m/z: 480, 482 (M–H)$^-$

EXAMPLE 9

After the mixed solution 500 ml of rat liver microsome treated by phenobalital (2 mg protein/ml),potassium phosphate buffer(pH 7.4), (2R)-5-(carboxymethoxy)-2-[(N,N-diphenylcarba moyloxy)methyl]-2-hydroxy-1,2,3,4-tetrahydronaphthalene (0.1 M), 1 mM NADPH generating system [NADP (nicotinamide adenine dinucleotide phosphate, 1 mM), glucose-6-Phosphate (5 mM) glucose-6-Phosphate dehydrogenase (1 unit/ml), $MgCl_2$ (5 mM)]was incubated at 37° C. for one hour, the reaction mixture was adjusted at pH3 with 12N HCl, extracted with ethyl acetate 800 ml for 20 minutes, centrifuged at 3000 rpm for 5 minutes. The sapalated organic layer was evaporated under 40° C. until dryness. The little amount of the mixed solution MeOH/AcOH (100/1,v/v) was added to the residue and the solution was injected into HPLC (HPLC condition; varian 5000LC pump, Capcelle Pak C18 SG120 5 μm (10×250 mm) mobile phase (A: acetonitrile, B: 20 mM H3PO4-KH2PO4 (pH2.5), flow rate 5.3 ml/min, Gradient A% 30% (0–17 min.) 47%(17–17.1 min.), 80%(17.1–19 min.), 30% (19–19.1 min.)))to give (2R)-5-(Carboxymethoxy)-2-hydroxy-2-{[(N-(4-hydroxyphenyl)-N-phenyl)carbamoyloxy]methyl}-1,2,3,4-tetrahydronaphthalene (18 mg).

IR (CHCl$_3$): 3401, 1724, 1708 cm$^{-1}$

NMR (CDCl$_3$, δ): 1.6–2.0 (2H, m), 2.6–3.0 (4H, m), 4.14 (2H, s), 4.65 (2H, s), 6.57 (1H, d, j=8 Hz), 6.7–6.9 (2H, m), 7.0–7.4 (9H, m)

Mass: 464 (M$^+$)

What is claimed is:

1. A compound of the formula:

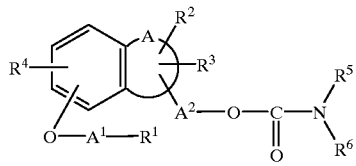

wherein $R^1$ is carboxy or protected carboxy, $R^2$ and $R^3$ are each independently hydrogen, hydroxy or protected hydroxy, $R^4$ is hydrogen or halogen, $R^5$ is aryl substituted with halogen, amino, hydroxy, $R^6$ is aryl optionally substituted with halogen, hydroxy or protected hydroxy, $A^1$ and $A^2$ are each independently lower alkylene, and

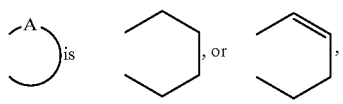

or its salt.

2. A compound of claim 1, wherein $R^1$ is carboxy or esterified carboxy, $A^1$ is $C_1$–$C_3$ alkylene, and $A^2$ is bond or $C_1$–$C_3$ alkylene.

3. A compound of claim 2, wherein $R^1$ is carboxy or lower alkoxycarbonyl, $R^2$ is hydroxy, $R^3$ is hydrogen or hydroxy, $R^4$ is hydrogen or halogen, $A^1$ is methylene, and $A^2$ is methylene.

4. A compound of claim 3, which is a compound of the formula:

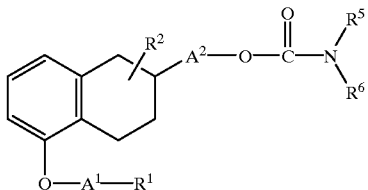

wherein $R^1$ is carboxy or lower alkoxycarbonyl, $R^2$ is hydroxy, $R^5$ is aryl substituted with halogen, hydroxy or protected hydroxy, $R^6$ is aryl optionally substituted with halogen, hydroxy or protected hydroxy, $A^1$ is methylene, and $A^2$ is methylene.

5. A compound of claim 4, which is sodium {{(2R)-2-{[N,N-di(4-fluorophenyl)carbamoyloxy]-methyl}-2-hydroxy-1,2,3,4-tetrahydro-5-naphthyl}oxy}-acetate.

6. A process for preparing a compound of the formula:

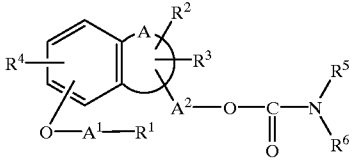

wherein $R^1$ is carboxy or protected carboxy, $R^2$ and $R^3$ are each independently hydrogen, hydroxy or protected hydroxy, $R^4$ is hydrogen or halogen, $R^5$ is aryl substituted with halogen, hydroxy or protected hydroxy, $R^6$ is aryl optionally substituted with halogen, hydroxy or protected hydroxy, $A^1$ and $A^2$ are each independently lower alkylene, and

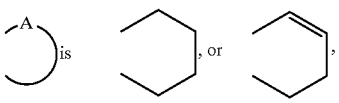

or its salt, that comprises (1) reacting a compound of the formula:

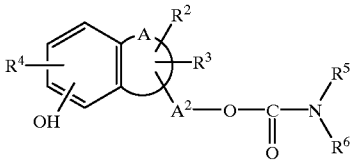

or its salt with a compound of the formula:

$$X^1—A^1R^1$$

or its salt to give a compound of the formula:

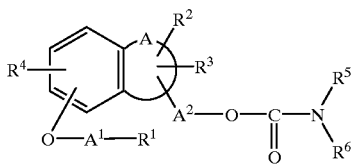

or its salt, wherein in the above formulas,
R$^1$, R$^2$, R$^3$, R$^4$, R$^5$, R$^6$, A$^1$, A$^2$ and

are each as defined above, and

X$^1$ is a leaving group;
(2) subjecting a compound of the formula:

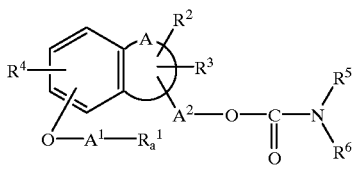

or its salt to an elimination reaction to give a compound of the formula:

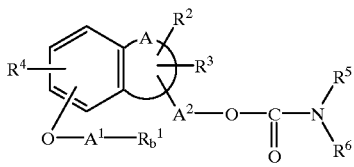

or its salt, wherein in the above formulas,
R$^1$, R$^2$, R$^3$, R$^4$, R$^5$, R$^6$, A$^1$, A$^2$ and

are each as defined above,

R$_a^1$ is protected carboxy, and
R$_b^1$ is carboxy; or (3) reacting a compound of the formula:

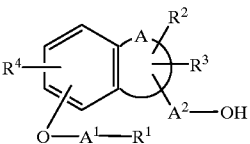

or its salt with a compound of the formula:

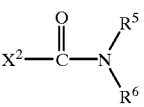

or its salt to give a compound of the formula:

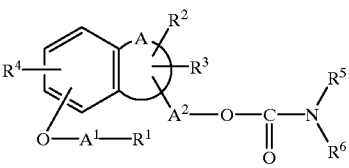

or its salt,
wherein in the above formulas,
R$^1$, R$^2$, R$^3$, R$^4$, R$^5$, R$^6$, A$^1$, A$^2$

and are each as defined above, and
X$^2$ is a leaving group.

7. A pharmaceutical composition which comprises, as an active ingredient, a compound of claim 1 or a pharmaceutically acceptable salt thereof in admixture with pharmaceutically acceptable carriers.

8. The composition of claim 7 that is a prostaglandin I$_2$ agonist.

9. A method for treating or preventing arterial obstruction, restenosis or ischemic complications after coronary angioplasty, arteriosclerosis, cerebrovascular disease, hepatitis, hepatic insufficiency, hepatic cirrhosis, ischemic heart disease, or dermatosis that comprises administering a pharmaceutically effective amount of a compound of claim 1 or a pharmaceutically acceptable salt thereof to a human or an animal.

10. A process for preparing a pharmaceutical composition which comprises admixing a compound of claim 1 or a pharmaceutically acceptable salt thereof with a pharmaceutically acceptable carrier.

11. A method for agonising the effect of PGI$_2$ comprising administering an effective amount of the compound of claim 1 to a subject in need thereof.

12. A method for inhibiting platelet aggregation, vasodilation or hypertension comprising administering an effective amount of the compound of claim 1 to a subject in need thereof.

* * * * *